(12) United States Patent
Boomgaarden

(10) Patent No.: US 8,459,868 B2
(45) Date of Patent: Jun. 11, 2013

(54) PORTABLE X-RAY MACHINE WITH DRIVE WHEEL SUSPENSION

(75) Inventor: Jonathan Carl Boomgaarden, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 261 days.

(21) Appl. No.: 12/953,218

(22) Filed: Nov. 23, 2010

(65) Prior Publication Data

US 2012/0128130 A1 May 24, 2012

(51) Int. Cl.
*H05G 1/02* (2006.01)
(52) U.S. Cl.
USPC ............................................ 378/198
(58) Field of Classification Search
USPC .......................................... 378/193, 197, 198
See application file for complete search history.

(56) References Cited

U.S. PATENT DOCUMENTS

| 5,503,416 A | 4/1996 | Aoki et al. |
| 2002/0146088 A1 | 10/2002 | Riemer et al. |
| 2005/0179878 A1 | 8/2005 | Ohtsuka |
| 2008/0008290 A1 | 1/2008 | Tybinkowski et al. |

FOREIGN PATENT DOCUMENTS

| GB | 794937 A | 5/1958 |
| WO | 2011075232 A1 | 6/2011 |

OTHER PUBLICATIONS

Search Report and Written Opinion from corresponding EP Application No. 11189442.4, dated Feb. 28, 2012.

*Primary Examiner* — Jurie Yun
(74) *Attorney, Agent, or Firm* — Fletcher Yoder, P.C.

(57) ABSTRACT

In one embodiment, a portable X-ray imaging system is provided with a base unit and at least one front wheel on which the base unit is mounted. The base unit is also mounted on a pair of rear wheels. The imaging system is provided with a suspension system coupled to the base unit and to the rear wheels. The suspension system is arranged to permit flexible movement of the base unit and the rear wheels with respect to one another.

20 Claims, 4 Drawing Sheets

PORTABLE X-RAY MACHINE WITH DRIVE WHEEL SUSPENSION

BACKGROUND OF THE INVENTION

The subject matter disclosed herein relates to a portable X-ray imaging system and more particularly to a drive wheel suspension system for the portable X-ray imaging system.

In the hospital setting, mobile radiographic exams are performed on patients difficult to move or incapable of being moved. Also, in tertiary care medical centers, mobile radiographic exams represent a significant percentage of radiographic exams performed.

To perform mobile radiographic exams, a mobile radiographic imaging system, such as a portable X-ray imaging system, may be used. Mobile radiographic imaging systems may employ rigidly attached wheels positioned to allow an operator to move the imaging system from one location to another. With rigidly attached wheels, high shock loading may occur when the imaging system is pushed between locations due to the weight of the imaging system. Likewise, high shock loading may be accompanied by loud noises, and may cause vibrations and abnormally large, sudden loads on the system components, which can damage the drive trains and wheels, as well as circuit boards and other components.

Therefore, it may be desirable to reduce shock loading, which may result in quieter movement of the imaging system, improved operator comfort during movement, and decreased damage to the imaging system components.

BRIEF DESCRIPTION OF THE INVENTION

In one embodiment, a portable X-ray imaging system is provided. The portable X-ray imaging system includes a base unit, at least one front wheel on which the base unit is mounted, a pair of rear wheels on which the base unit is mounted, and a suspension system coupled to the base unit and to the rear wheels and configured to permit flexible movement of the base unit and the rear wheels with respect to one another.

In another embodiment, a portable X-ray imaging system is provided. The portable X-ray imaging system includes a base unit, an X-ray source moveable between a transport position and an imaging position, at least one front wheel on which the base unit is mounted, and a rear wheel assembly including a pair of rear wheels on which the base unit is mounted. The portable X-ray imaging system also includes a suspension system coupled to the base unit and to the rear wheel assembly and configured to permit flexible movement of the base unit and the rear wheel assembly with respect to one another when the X-ray source is in the transport position, and to limit movement of the base unit when the X-ray source is in the imaging position.

In a third embodiment, a method for making a portable X-ray imaging system is provided. The method includes coupling a base unit to at least one front wheel on which the base unit is mounted, coupling the base unit to a rear wheel assembly comprising a pair of rear wheels on which the base unit is mounted, and coupling a suspension system between the base unit and to the rear wheel assembly. The suspension system is configured to permit flexible movement of the base unit and the rear wheel assembly with respect to one another.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
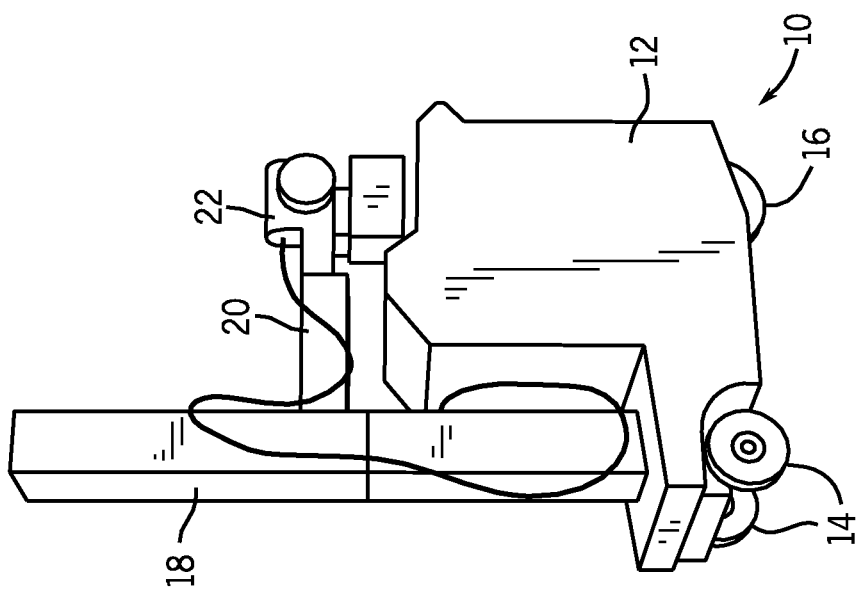
FIG. 1 is a perspective view of a portable X-ray system in a transport position.

FIG. 1 depicts a portable X-ray system 10 in a transport position. The portable X-ray system 10 includes a base unit 12 with front wheels 14 and drive rear wheels 16. The wheels 14, 16 are mounted to the base unit 12 enabling the X-ray system 10 to be moved. An operator may move the X-ray system 10 by pushing on handles that may be located on the back end of the base unit 12 over the drive rear wheels 16. In certain designs, the operator may guide the system as it moves, but need not actually push the unit, which is instead propelled by drive motors associated with the wheeled support structure. In the illustrated embodiment, the front wheels 14 are caster wheels which may swivel as the portable X-ray system 10 turns during transport. Furthermore, the front wheels 14 may be spring loaded castor wheels to provide front wheel suspension; such wheels are available commercially from Albion Incorporated of Albion, Mich. The base unit 12 may include electronic circuitry and a power supply, such as one or more batteries. The power supply may provide power to operate the drive rear wheels 16. For example, the power supply may drive one or more motors that may be attached to the rear wheels. It may be noted that the batteries (or a separate power supply or power cable) may also serve to provide power for imaging sequences performed once the system is positioned at an imaging location (e.g., beside a bed or other patient support).

A mast 18 is coupled to the base unit 12 and has a boom 20 extending outwardly, generally perpendicular to the mast 18. The mast 18 and/or the boom 20 may swivel on the base unit 12 to a position for radiographic exams to be performed, i.e., an imaging position. An X-ray source 22 is coupled to the boom 20 and enables the X-ray system 10 to produce X-rays needed to acquire image data during a radiographic exam. Cables may connect the X-ray source 22 to power and control circuitry located in the base unit 12. As may be appreciated, the base unit 12, mast 18, boom 20 and X-ray source 22 may create a heavy load on the wheels 14, 16. Therefore, the portable X-ray system 10, in accordance with the innovations described in this disclosure, may include a suspension system attached to the drive rear wheels 16 to reduce shock loading, vibration, and shaking that may occur when the system is being moved.

Figure 2:
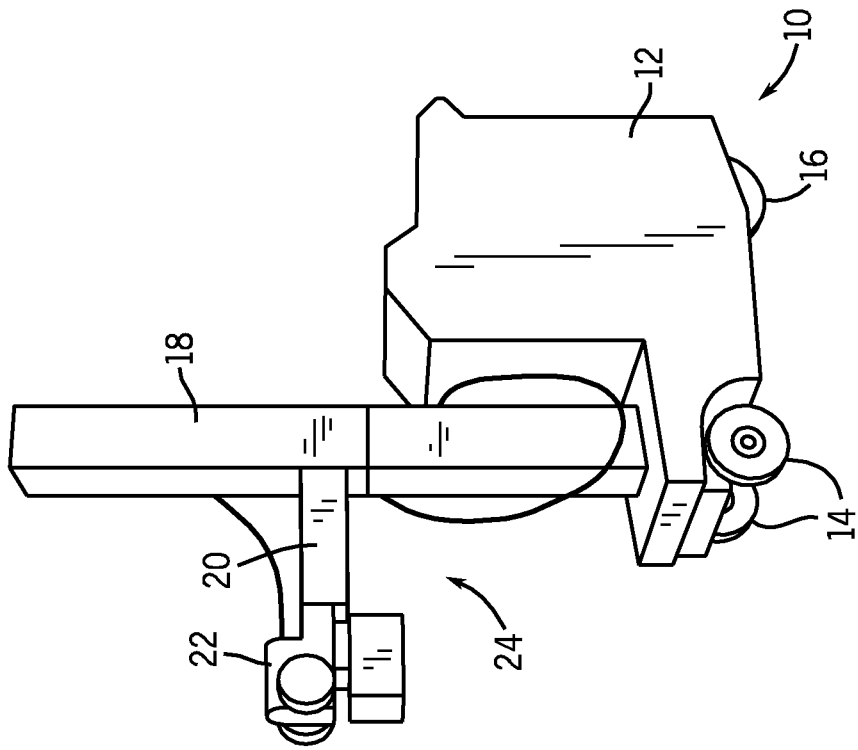
FIG. 2 is a perspective view of the portable X-ray system of FIG. 1 in an imaging position.

FIG. 2 is an illustration depicting the portable X-ray system 10 of FIG. 1 in an imaging position 24. In this position, as opposed to the transport position, the mast 18 and/or the boom 20 is rotated 180 degrees from the transport position to cause the boom 20 to extend away from the X-ray system 10. The boom 20 and/or the X-ray source 22 may be adjusted toward or away from the mast 18 to properly position the X-ray source 22 over a patient. With the boom 20 and the X-ray source 22 extending away from the base unit 12, the center of gravity shifts away from the drive rear wheels 16 and toward the front wheels 14, thus decreasing the load on the drive rear wheels 16. As such, as described below, if the portable X-ray system 10 includes a suspension system attached to the drive rear wheels 16, the decreased load on the rear wheels 16 may force the suspension system against a stop, and thus provide a stable platform during imaging.

Figure 3:
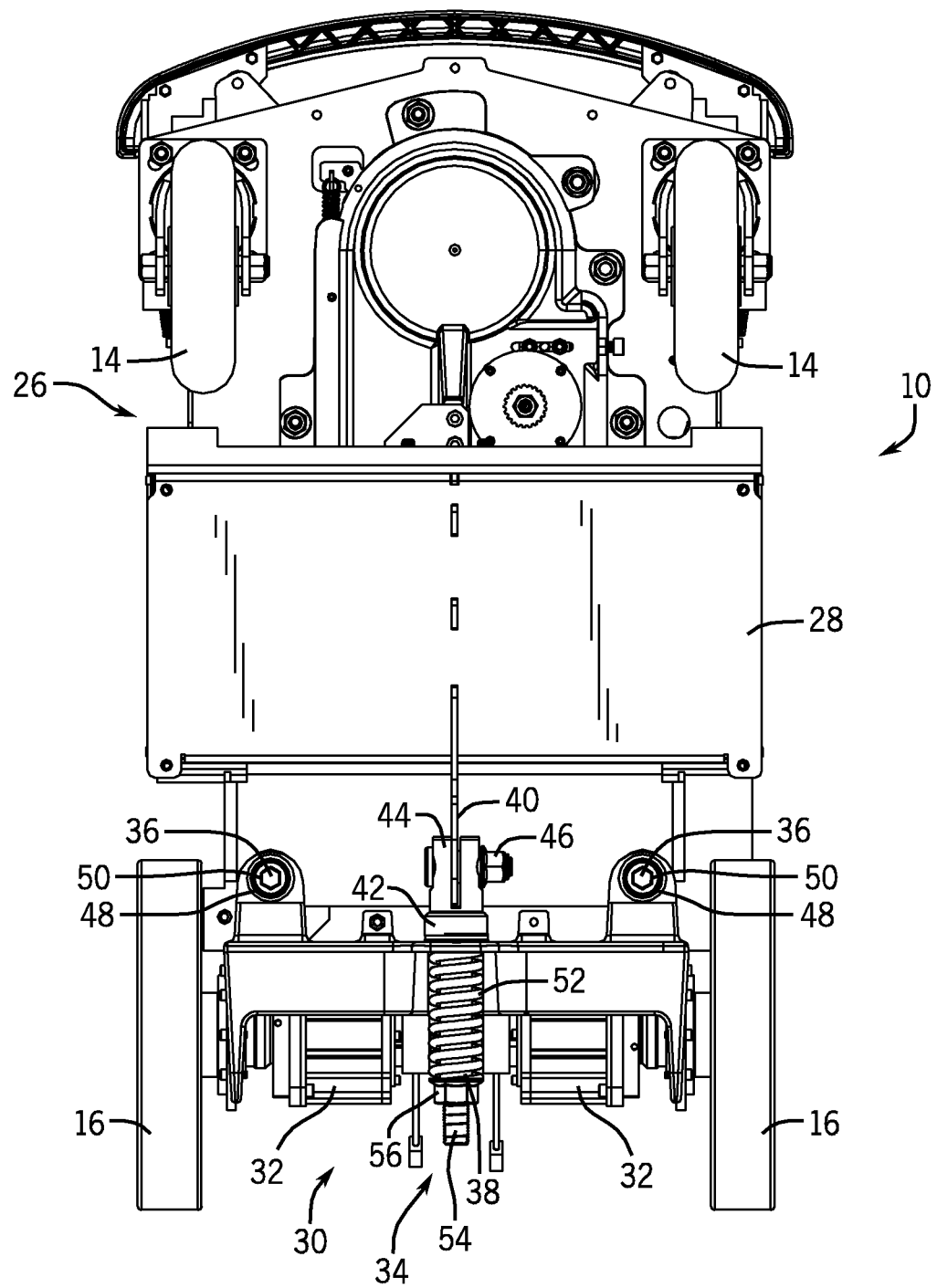
FIG. 3 is an underside plan view of an embodiment of the portable X-ray system of FIG. 1 with a suspension system.

FIG. 3 is an underside plan view of an embodiment of the portable X-ray system 10 of FIG. 1 with a suspension system. The front wheels 14 are mounted to a carriage frame 26 which includes a battery compartment 28. Also mounted to the carriage frame 26 is a rear wheel assembly 30. The wheel assembly 30 includes the drive rear wheels 16 and motors 32. The motors 32 are coupled to the drive rear wheels 16 and may drive the rear wheels in rotation to propel the X-ray system 10. The battery compartment 28 may hold one or more batteries that provide power to the motors 32.

A suspension assembly 34 provides suspension to the portable X-ray system 10. The rear wheel assembly 30 is attached to the carriage frame 26 at pivot points 36. The pivot points 36 aid in suspension by enabling the rear wheel assembly 30 to move flexibly in relation to the carriage frame 26. Although two pivot points 36 are illustrated, fewer or more pivot points may be used based on the configuration of the portable X-ray system 10. For example, if the width of an X-ray system increases, the number of pivot points may increase.

The suspension assembly 34 includes a spring assembly 38 attached to a tang 40 extending out of the battery compartment 28. The spring assembly 38 includes a pivoting spring rod 42 with a clevis end 44. The tang 40 is secured inside the clevis end 44 of the pivoting spring rod 42 with a pin 46, thus connecting the suspension assembly 34 to the carriage frame 26. Such an attachment allows the tang 40 latitude to move within the clevis end 44 of the pivoting spring rod 42. Other embodiments may use different linking hardware to enable flexible movement between the rear wheel assembly 30 and the carriage frame 26.

Pivot bushings 48 with bolts 50 extending through them secure the rear wheel assembly 30 to the carriage frame 26 and create the pivot points 36. The pivot bushings 48 may be made of natural rubber, silicon rubber, or another material that enables pivoting between the rear wheel assembly 30 and the carriage frame 26. Alternatively, the pivot bushings 48 may include a combination of rubber-like or resilient material and metal. For example, the pivot bushings 48 may be fabricated center bonded mounts, available commercially from Lord Corporation of Cary, N.C.

In the illustrated embodiment, the suspension assembly 34 includes a spring 52 positioned around the pivoting spring rod 42 and moved toward the clevis end 44 of the rod 42 to expose a threaded end 54. A nut 56 securely tightened over the threaded end 54 secures the spring 52 in place. The spring 52 is oriented to extend generally in a direction parallel to a horizontal plane. The spring 52 is depicted as a compression spring, however, other springs such as belleville, volute, or cantilever springs may be used in other embodiments. Furthermore, the spring 52 may be composed of stainless steel, chrome silicon, titanium, or other suitable metal.

It should be noted that, while the present discussion describes a common or single suspension system for both rear wheels, in alternative configurations, the rear wheels may be independently or semi-independently suspended. For example, in other contemplated embodiments multiple springs may be mounted on multiple pivoting spring rods with each spring rod attached to a tang, or certain embodiments may have springs mounted on each wheel so that each wheel independently provides suspension to the X-ray system 10. As with the illustrated embodiment, such arrangements may use differently configured suspension systems as well, and that described herein should be understood as one possible configuration.

In a transport position, the load of the X-ray system 10 may force the carriage frame 26 downward. This downward load may cause the carriage frame 26 to press against the pivot points 36 and the clevis end 44 of the pivoting spring rod 42. The rear wheel assembly 30 may pivot at the pivot points 36 by compressing the material of the pivot bushings 48. In addition, the spring 52 may be compressed between the rear wheel assembly 30 and the nut 56 as the pivoting spring rod 42 is pulled toward the carriage frame 26. When this happens the tang 40 is enabled to pivot about the clevis end 44. As the load on the carriage frame 26 increases, the spring 52 may compress more. Conversely, as the load decreases, the spring 52 may become less compressed. Furthermore, when the X-ray system is transitioned to the imaging position the suspension assembly 34 may not compress the spring 52, but instead may cause the suspension system to rest in a normal position held against a stop.

The suspension assembly 34 may operate in a similar manner when the X-ray system 10 travels over bumps or uneven surfaces. The uneven surfaces may produce high shock loading which causes the spring 52 of the suspension assembly 34 to compress and decompress back and forth for absorption of the shock. While the suspension assembly 34 absorbs the shock, noise and X-ray system 10 vibration may decrease.

Figure 4:
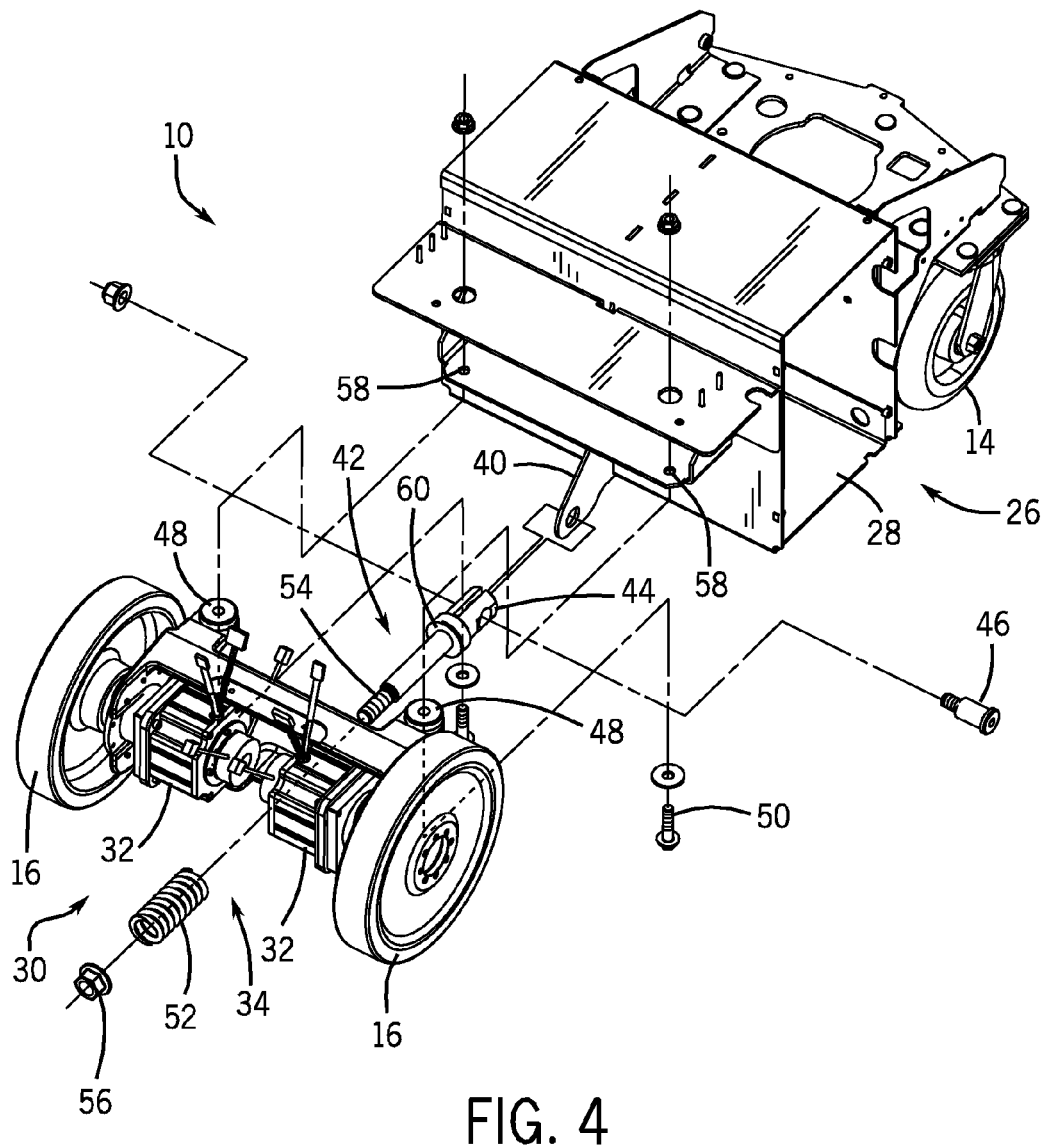
FIG. 4 is an exploded perspective view of an embodiment of the portable X-ray system of FIG. 3.

FIG. 4 is an exploded perspective view of an embodiment of the portable X-ray system 10 of FIG. 3 depicting how the carriage frame 26, rear wheel assembly 30, and suspension assembly 34 are assembled. The carriage frame 26 includes apertures 58 on a structure extending perpendicular to the battery compartment 28, as illustrated. To attach the carriage frame 26 to the rear wheel assembly 30, the apertures 58 are positioned on top of the pivot bushings 48. Bolts 50 are inserted through the pivot bushings 48 and the apertures 58, and secured with nuts to hold the carriage frame 26 to the rear wheel assembly 30.

A cushion washer 60 is placed on the pivoting spring rod 42 near the clevis end 44 so that the cushion washer 60 rests against a portion of the rear wheel assembly 30 when assembled. The pivoting spring rod 42 is attached to the rear wheel assembly 30 by inserting it through the rear wheel assembly 30. The spring 52 slides over the pivoting spring rod 42 and the nut 56 secures the spring 52 in place. The pivoting spring rod 42 is connected to the carriage frame 26 by positioning the tang 40 within the clevis end 44 of the pivoting spring rod 42 and inserting the pin 46. The pin 46 holds the clevis end 44 of the rod 42 to the tang 40 via a nut secured to the end of the pin 46.

The cushion washer 60 may enable the suspension assembly 34 to cushion the impact that may occur between the rear wheel assembly 30 and the pivoting spring rod 42 when the suspension assembly 34 moves against a stop, such as when the X-ray system 10 is moved from the transport position to the imaging position. The cushion washer 60 may be made of natural rubber, silicon rubber, or any other suitable material.

Combined together, the rear wheel assembly 30, the cushion washer 60, and the clevis end 44 of the pivoting spring rod 42 may operate as the stop for the suspension assembly 34.

When operating as the stop, the rear wheel assembly 30 is pressed against the cushion washer 60 which is pressed against the clevis end 44 of the pivoting spring rod 42, thus inhibiting the spring 52 from further decompression. The stop inhibits movement of the carriage frame 26 with respect to the rear wheel assembly 30. Furthermore, the suspension assembly 34 may press the pivoting spring rod 42 against the stop when the load of the portable X-ray system 10 exerts sufficiently less force on the rear wheel assembly 30, such as when the X-ray system 10 is moved to an imaging position.

Figure 5:
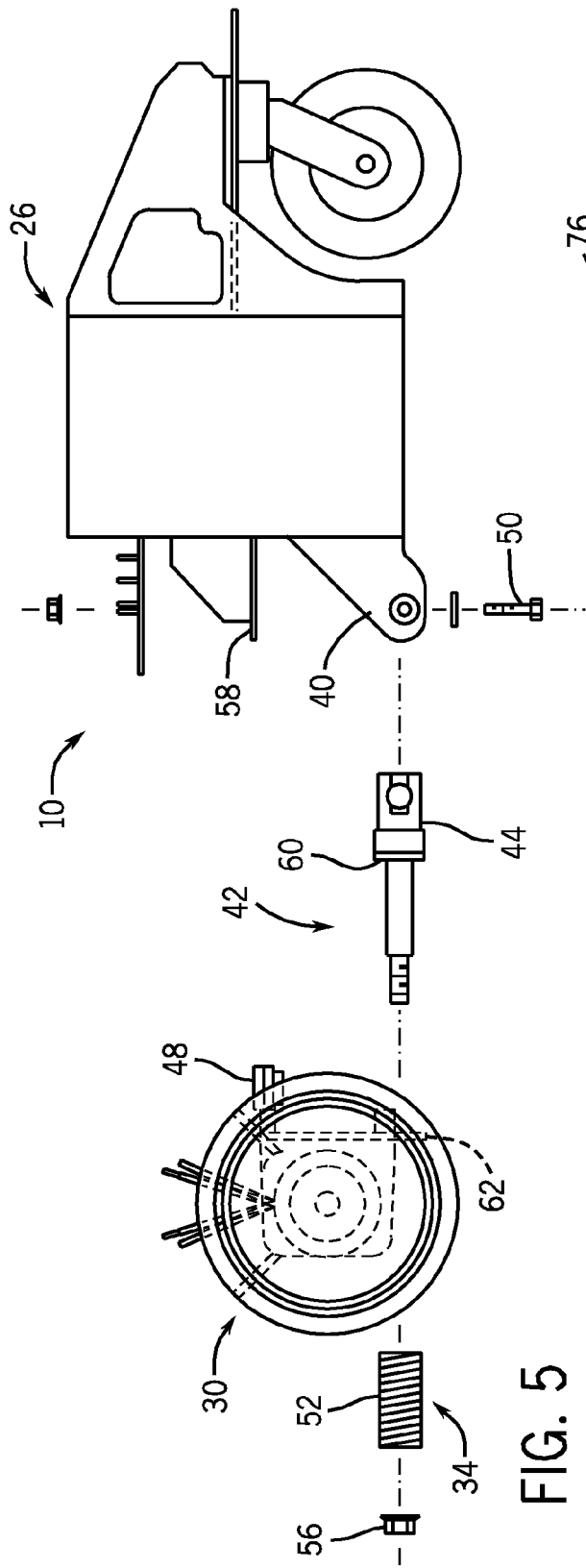
FIG. 5 is an exploded side elevation view of an embodiment of the portable X-ray system of FIG. 4.

FIG. 5 is an exploded side view of an embodiment of the portable X-ray system 10 of FIG. 4 depicting how the carriage frame 26, rear wheel assembly 30, and suspension assembly 34 are assembled. As previously described in relation to FIG. 4, bolts 50 are inserted through the pivot bushings 48 and the apertures 58 while nuts attach to the bolts 50 to secure the carriage frame 26 to the rear wheel assembly 30.

The cushion washer 60 is placed on the pivoting spring rod 42 near the clevis end 44 so that the cushion washer 60 rests against a lower extension 62 of the rear wheel assembly 30 when assembled. The pivoting spring rod 42 is attached to the rear wheel assembly 30 by inserting it through the lower extension 62. The spring 52 slides over the pivoting spring rod 42 and the nut 56 secures the spring 52 in place. Thus, the spring 52 is compressed between the nut 56 and the lower extension 62, and may be preloaded by appropriately locating the nut on the spring rod. Again, the pivoting spring rod 42 is connected to the carriage frame 26 by positioning the tang 40 within the clevis end 44 of the pivoting spring rod 42 and inserting the pin 46. The pin 46 is held in place via a nut.

As the load on the carriage frame 26 increases, the rear wheel assembly 30 may press downward at the pivot bushings 48. The rear wheel assembly 30 may pivot at the pivot bushings 48 and the pivoting spring rod 42 may be pulled toward the carriage frame 26 which results in the nut 56 compressing the spring 52 between itself and the lower extension 62. Conversely, when the load on the carriage frame 26 decreases, downward force may be removed from the pivot bushings 48. When enough weight is removed, the suspension system may rest in a normal position where the spring 52 is decompressed as much as possible. In such a position, the lower extension 62 rests against the cushion washer 60, which acts as a stop (or it may be said that the lower extension 62 acts as a stop for the spring rod). The suspension system may operate in a similar manner when the rear wheel assembly 30 travels over bumps or uneven surfaces. For example, uneven surfaces may cause a quick shock that the suspension system absorbs through compression and decompression of the spring 52.

Figure 6:
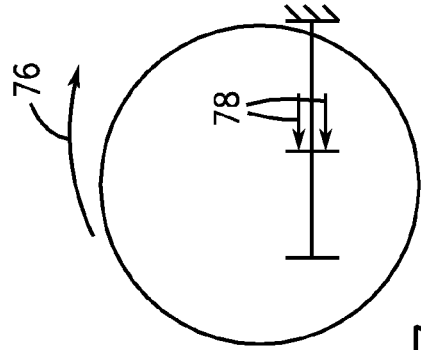
FIG. 6 is a diagrammatical view depicting compression length changes of the suspension system of FIG. 5 when the rear wheel assembly moves from a normal position to a suspension position.

FIG. 6 is a kinematic diagram depicting compression length changes (somewhat exaggerated) of the suspension system of FIG. 5 when the rear wheel assembly moves from a normal position 64 to a suspension position 66. The rear wheel assembly begins at the normal position 64, then as the assembly pivots and the spring compresses, the rear wheel assembly moves upward to a suspension position 66 (or it may be said that the base unit moves downwardly). Such an upward movement may occur as the portable X-ray system moves over bumps or objects in its path and the suspension system compresses its spring to compensate for these bumps.

As illustrated, in the normal position 66, the spring has a spring length l, as indicated by reference numeral 68. The distance from the end of the spring to the stop is denoted as abutment-to-pin length L, as also indicated by reference numeral 70. Alternatively, in the suspension position 66 the compressed spring has a shorter, compressed length l', as indicated by reference numeral 72. The compressed abutment-to-pin length is then L', as indicated by reference numeral 74. As may be appreciated, the combined length of the spring length l and the abutment-to-pin length L will be equal to the combined length of compressed spring length l' and the compressed abutment-to-pin length L'.

Figure 7:
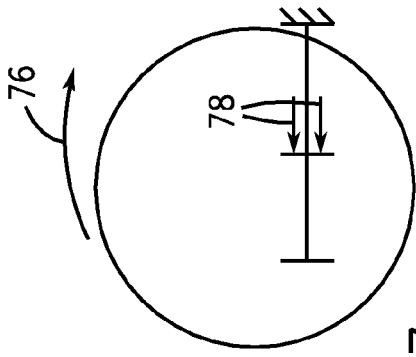
FIG. 7 is a diagrammatical view depicting a moment of the suspension system of FIG. 5 when the portable X-ray system is in the imaging position.

FIG. 7 is a view depicting a moment 76 of the suspension system of FIG. 5 when the portable X-ray system is in the imaging position. With the moment 76, a force 78 is exerted pressing the pivoting spring rod toward the lower extension of the rear wheel assembly, holding it firmly in place while imaging takes place. In other words, the suspension system is forced against the stop, thereby providing a stable position.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A portable X-ray imaging system, comprising:
   a base unit comprising user operable controls for controlling motion of the base unit;
   at least one front wheel on which the base unit is mounted;
   a pair of rear wheels on which the base unit is mounted; and
   a suspension system coupled to the base unit and to the rear wheels and configured to permit flexible movement of the base unit and the rear wheels with respect to one another.

2. The system of claim 1, wherein the rear wheels comprise an assembly with at least one drive motor for driving the rear wheels in rotation to propel the base unit.

3. The system of claim 1, wherein the suspension system comprises at least one spring.

4. The system of claim 3, wherein the spring comprises a compression spring that is compressed to allow for relative movement between the base unit and the rear wheels.

5. The system of claim 4, wherein the suspension system comprises a stop configured to limit movement of the base unit with respect to the rear wheels.

6. The system of claim 5, wherein the base unit supports an X-ray source, and wherein the suspension system is configured to limit movement of the base unit via the stop when the X-ray source is moved to an imaging position.

7. The system of claim 5, comprising at least one cushion element configured to cushion impact when movement of the base unit with respect to the rear wheels is limited via the stop.

8. A portable X-ray imaging system, comprising:
   a base unit comprising user operable controls for controlling motion of the base unit;
   an X-ray source moveable between a transport position and an imaging position;
   at least one front wheel on which the base unit is mounted;
   a rear wheel assembly comprising a pair of rear wheels on which the base unit is mounted; and
   a suspension system coupled to the base unit and to the rear wheel assembly and configured to permit flexible movement of the base unit and the rear wheel assembly with respect to one another when the X-ray source is in the transport position, and to limit movement of the base unit when the X-ray source is in the imaging position.

9. The system of claim 8, wherein the rear wheel assembly comprises at least one drive motor for driving the rear wheels in rotation to propel the base unit.

10. The system of claim 8, wherein the suspension system comprises at least one spring.

11. The system of claim 10, wherein the spring comprises a compression spring that is compressed to allow for relative movement between the base unit and the rear wheel assembly.

12. The system of claim 11, wherein the suspension system comprises a stop configured to limit movement of the base unit with respect to the rear wheel assembly.

13. The system of claim 12, comprising at least one cushion element configured to cushion impact when movement of the base unit with respect to the rear wheel assembly is limited via the stop.

14. A method for making a portable X-ray imaging system, comprising:
   coupling a base unit to at least one front wheel on which the base unit is mounted, wherein the base unit comprises user operable controls for controlling motion of the base unit;
   coupling the base unit to a rear wheel assembly comprising a pair of rear wheels on which the base unit is mounted; and
   coupling a suspension system between the base unit and to the rear wheel assembly, the suspension system being configured to permit flexible movement of the base unit and the rear wheel assembly with respect to one another.

15. The method of claim 14, comprising coupling at least one drive motor to the rear wheel assembly for driving the rear wheels in rotation to propel the base unit.

16. The method of claim 14, wherein the suspension system comprises at least one spring.

17. The method of claim 16, wherein the spring comprises a compression spring that is compressed to allow for relative movement between the base unit and the rear wheel assembly.

18. The method of claim 17, wherein the suspension system comprises a stop configured to limit movement of the base unit with respect to the rear wheel assembly.

19. The method of claim 18, wherein the base unit supports an X-ray source, and wherein the suspension system is configured to limit movement of the base unit via the stop when the X-ray source is moved to an imaging position.

20. The method of claim 18, comprising at least one cushion element configured to cushion impact when movement of the base unit with respect to the rear wheel assembly is limited via the stop.

* * * * *